United States Patent [19]

Edwards et al.

[11] Patent Number: 5,683,894

[45] Date of Patent: Nov. 4, 1997

[54] RECOMBINANT NERVE GROWTH FACTOR

[75] Inventors: Robert H. Edwards; William J. Rutter, both of San Francisco, Calif.

[73] Assignee: University of California, Alameda, Calif.

[21] Appl. No.: 666,550

[22] Filed: Mar. 7, 1991

Related U.S. Application Data

[63] Continuation of Ser. No. 188,045, Apr. 29, 1988, abandoned.

[51] Int. Cl.$^6$ .............................. C12P 21/06; C12N 5/08; C12N 15/18; C07K 14/48

[52] U.S. Cl. .................. 435/69.4; 435/240.1; 435/320.1; 536/23.1; 530/399

[58] Field of Search .......................... 435/68, 70, 172.3, 435/255, 254, 320, 69.1, 69.4, 320.1, 240.1; 935/37; 536/27, 23.1; 530/399

[56] References Cited

FOREIGN PATENT DOCUMENTS

| 196056 | 10/1956 | European Pat. Off. ................ 435/68 |
|---|---|---|
| 0121338 | 2/1984 | European Pat. Off. . |

OTHER PUBLICATIONS

Scott et al *Nature* vol. 302 pp. 538–540 1983 "Isolation and Nucleotide Sequence of a CDNA Encoding the Precursor of Nerve Growth Factor".
Angeletti et al., *Biochemistry* (1973) 12:100–115.
Berger et al., *Proc. Nat. Acad. Sci.* (1977) 74:3647–3651.
Darling et al., "Cold Spring Harbor Symposia On Quantitative Biology " (1983) pp. 427–434.
Edwards et al., "Processing of the Native NGF Precursor to Form Biologically Active NGF" (unpublished).
Fischer et al., *Nature* (1987) 329:65–68.
Hofer et al., *Nature* (1988) 331:261–262.
Lindholm et al., *Nature* (1987) 330:658–659.
Saboori et al., *Biochemistry* (1986) 25:5565–5571.
Edwards et al., *Nature* (1986) 319:784–787.
Heijne, *Nucleic Acids Res.* (1986) 14:4683–4690.
Selby et al., *Mol. Cell. Biol.* (1987) 7:3057–3064.

*Primary Examiner*—Vasu S. Jagannathan
*Assistant Examiner*—K. Cochrane Carlson
*Attorney, Agent, or Firm*—Morrison & Foerster LLP

[57] ABSTRACT

A method for producing pure, active, mature recombinant Nerve Growth Factor-beta is disclosed, as is the protein so produced.

5 Claims, No Drawings

RECOMBINANT NERVE GROWTH FACTOR

This application is a continuation of application Ser. No. 07/188,045, filed 29 Apr. 1988, now abandoned.

This invention was made with United States Government support under Grant No. NS-01146 with the National Institutes of Health and the University of California. The United States Government has certain rights in this invention.

TECHNICAL FIELD

This invention relates to the molecular biology of cellular growth factors and recombinant DNA technology. More specifically, this invention relates to nerve growth factor (NGF), its therapeutic use, and processes for producing active NGF.

BACKGROUND

Nerve growth factor is a protein which regulates the survival, differentiation and growth of specific neuronal populations in vivo (see e.g., M. M. Hofer et al, *Nature* (1988) 331:261–62). NGF is expressed in a variety of somatic cells, and is found in many vertebrate species. A particularly convenient source of NGF is the submaxillary gland of male mice. However, there are no practical natural sources of NGF, particularly human NGF, suitable for human therapeutic use.

The murine NGF is expressed as a 7S complex, containing the NGF-alpha, beta, and gamma chains. NGF-beta is a dimer of two identical 118 amino acid (aa) chains, and is apparently solely responsible for the observed biological activity of NGF. NGF-gamma is a serine protease of the kallikrein protease group (by amino acid sequence homology), which binds to NGF-beta stoichiometrically. NGF-alpha also shows high homology with the kallikrein protease family and binds NGF-beta stoichiometrically, but displays no known catalytic activity. NGF-alpha is apparently inactive due to a point mutation in the active site of the protein.

In the peripheral nervous system, NGF regulates the survival and differentiation of sympathetic and sensory neurons. As several forms of hereditary neuropathy (e.g., familial dysautonomia) selectively affect these neuronal elements, NGF may have a role in treatment. Similarly, neuroblastoma is a childhood tumor which derives from sympathetic neurons. Since NGF promotes the differentiation of this cell type, it could prove useful in controlling tumor growth.

Following peripheral nerve injury, a variety of cells begin to synthesize NGF. It has recently been shown that Schwann cells secrete elevated levels of NGF following nerve injury, in response to interleukin-1 secreted by activated macrophages invading the lesion site (D. Lindholm, et al, *Nature* (1987) 330:658–59). NGF participates in the reestablishment of synaptic contact in severed tissues. Supplementation with exogenous NGF may facilitate the regenerative process and prevent poor outcomes, in which the nerves fail to reach their proper targets, or form abnormal connections with each other, producing a pain syndrome.

Cholinergic neurons in the CNS also depend on NGF for survival. One major cholinergic pathway, from the basal forebrain to the hippocampus (which responds to NGF), shows early, severe, relatively selective destruction in Alzheimer's disease. NGF may aid in the survival and function of this neuronal population and thus may provide an effective treatment for Alzheimer's disease. One study has already shown an improvement in the performance of senile rats in response to NGF (W. Fischer et al, *Nature* (1987) 329:65–68). In addition, there is some evidence that brain transplants performed for Parkinson's disease do not themselves account for all the observed clinical improvement, and may only serve to induce sprouting of adjacent host neurons. This suggests that transplantation releases local growth factors, which may be more important than the graft itself in ameliorating the condition.

Presently, NGF is prepared by purification from male mouse submaxillary gland. Although the resulting preparation is sufficiently pure for sequencing and laboratory experimentation, this source is not adequate or practical for large scale production. Additionally, purification of natural material does not provide for convenient modification (e.g., by site specific mutagenesis) or derivatization (e.g., by adding or removing carbohydrate groups, lipophilic groups, etc.). Further, only the murine NGF is of course obtained, raising the potential for immune reaction against heterologous protein if administered to humans. Thus, there exists a need to develop recombinant methods for preparing human NGF. If NGF-beta could be prepared alone, without the alpha and gamma subunits, this would also simplify the purification.

Many proteins are initially translated as larger precursor proteins, which may be active or inactive, and which are cleaved to release biologically active polypeptides. To produce the substantial amounts of human hormones required for medical use, frequently only the sequence of the mature form of the protein is expressed, bypassing the inactive precursor stage. This requires less processing of the product (with the attendant dangers of irreversible denaturation, inseparable product/precursor mixtures, and the unavoidable reduction of yield), and usually provides for a higher yield of active protein. This approach is especially preferred where prokaryotic or in vitro expression systems are employed for expressing eukaryotic proteins, due to the possibility that an essential (unknown) processing enzyme may be needed to cleave the precursor to its active form.

R. Angeletti et al, *Biochemistry*, (1973) 12:100–115 disclosed the amino acid sequence of mature murine NGF-beta (mouse 2.5S nerve growth factor), obtained by exhaustive degradative analysis.

E. Berger et al, *Proc Nat Acad Sci U.S.A.* (1977) 74:3647–51 radioactively labeled isolated mouse submaxillary glands and determined that NGF-beta can be identified first as an intermediate of 22,000 daltons (22 Kd), which is then processed to the 13 Kd mature NGF-beta. Both 22 Kd and 13 Kd proteins were identified in cell extracts using anti-NGF serum. Berger also demonstrated that treating the 22 Kd protein with NGF-gamma provides a 13 Kd protein, and disclosed that EGF binding protein also catalyses this conversion. However, no determination of biological activity was reported.

A. Saboori et al, *Biochemistry* (1986) 25:5565–71 disclosed the isolation from mouse submaxillary gland of a high molecular weight precursor (32 Kd), which is cleaved by NGF-gamma to provide NGF-beta. This 32 Kd protein is cleaved nonspecifically by trypsin and EGF-binding protein into at least 5 polypeptides. Another precursor is suggested, with a $M_r$ of 94–200 Kd, which is digested to a 70 Kd intermediate before resulting in the NGF-alpha, beta, and gamma subunits. This 94–200 Kd precursor is disclosed to exhibit weak activity in NGF bioassays and radioimmunoassays. However, subsequent cDNA and mRNA studies indicated that the upper $M_r$ band for NGF-beta precursors is about 35 Kd, and that such high molecular weight NGF precursors are most likely tightly-bound 7S NGF complexes (T. L. J. Darling et al, *Cold Spring Harbor Symposia On Quantitative Biology* (1983) 48:427–34). Darling et al found that when NGF-beta mRNA obtained from mouse submaxillary gland was translated in cell-free expression systems, anti-NGF IgG failed to precipitate significant amounts. Some precipitate ensued when the mRNAs were translated cell-free in the presence of anti-NGF IgG, however, no biological activity was reported.

R. H. Edwards et al, "Processing of the Native NGF Precursor to form Biologically Active NGF" (in press) have found that expression of the pro-NGF-beta polypeptide in cell-free systems results in an improperly-folded protein, which is degraded rather than cleaved to active form by NGF-gamma. A variety of other attempts to produce substantial amounts of biologically active NGF have also failed.

Thus, the preparation of active NGF-beta, other than by impractical purification from mouse submaxillary glands, has yet to be demonstrated. A need exists for a method of producing mature, active NGF-beta in sufficient quantity to enable its use in therapeutic treatment.

DISCLOSURE OF THE INVENTION

We have developed a method for preparing active NGF-beta by recombinant means, including a method for cleaving pro-NGF-beta to the active, mature NGF.

In another aspect of the invention, we have invented a therapeutic composition for treating neural disorders.

MODES OF CARRYING OUT THE INVENTION

A. Definitions:

The term "NGF-beta" refers to the pure, active, mature beta subunit of 7S NGF, and its equivalents. NGF-beta is a dimer of $M_r$ 26 Kd, and is not glycosylated. In terms of purity, the NGF-beta should be substantially free of contaminating proteins, containing no more than 25% foreign protein, preferably less than 15%, and most preferably less than 5%. Contaminating proteins are proteins present in crude preparations of NGF-beta prior to purification, or proteins naturally present with NGF-beta in vivo. The instant invention encompasses NGF-beta regardless of the species from which it is derived, and additionally includes "muteins," or proteins differing from the natural NGF sequence by the substitution or deletion of one or more amino acids (without adversely affecting the NGF activity), e.g., by site-specific mutagenesis. "Equivalents" of NGF-beta include derivatized forms of natural NGF-beta and muteins, for example by appropriate modification of amino acid side chains. One may chemically attach hydrophilic or lipophilic molecules to the side chains to adjust the solubility, stability, and biological distribution upon administration. Further, one may attach functional additions such as radioactive atoms, fluorescent dyes, enzymes (e.g., horse-radish peroxidase), monoclonal antibodies (or fragments thereof), cytotoxins (e.g., cisplatin, amphotericin B, ricin), and the like, e.g., for visualizing cell-type and receptor distribution, treating neuroblastomas, etc. Additionally, one may remove or modify the natural carbohydrate side chains, or express the NGF-beta in a heterologous system to provide for variant carbohydrate addition. Other variations and modifications will be apparent to those of ordinary skill in the art, and are to be considered within the scope of the instant invention.

The term "pro-NGF-beta" refers to any biological precursor which may be cleaved by NGF-gamma (inter alia) to provide mature, active NGF-beta. Thus for example, pro-NGF-beta includes the presently-known 34 Kd, 27 Kd, and 19 Kd precursors.

The term "neural disorder" as used herein refers to degenerative disorders of the nervous system which can respond to treatment with NGF-beta. Thus, diseases characterized by the loss and/or degeneration of neurons and nerves are within the scope of this invention. Exemplary disorders include without limitation Alzheimer's disease, Parkinson's disease, Lou Gehrig's disease, familial dysautonomia, and the like. Also considered within this definition is the treatment of nerve separation, e.g., where a nerve has been severed by trauma. Additionally, neuroblastoma, characterized by degenerate, undifferentiated nerve tumors, has been shown responsive to treatment with NGF-beta.

The term "effective amount" refers to the amount of NGF-beta needed to produce a desired manifestation of NGF activity. The precise amount will vary with the particular NGF-beta protein or derivative employed, the age and condition of the subject to be treated, and the nature and severity of the condition. However, the effective amount may be determined by one of ordinary skill in the art with only routine experimentation, following the methodology described herein.

The term "catalytic amount" refers to the amount of trypsin (or an equivalent protease) needed to cleave pro-NGF-beta into mature NGF-beta. A catalytic amount may be as little as, for example, 100 ng trypsin/50 uL of crude pro-NGF-beta.

The term "trypsin-like protease" refers to a proteolytic enzyme exhibiting a substrate specificity similar to that of trypsin. Functionally, a trypsin-like protease must be able to cleave pro-NGF-beta without substantially degrading the active portion of the molecule, and provide active, mature NGF-beta. Trypsin-like proteases may be selected from the various serine proteases, including kallikrein proteases. Presently preferred trypsin-like proteases are trypsin and NGF-gamma.

B. General Method

In general, a gene encoding pro-NGF-beta is first isolated from the desired species (e.g., human, murine, bovine, etc.) using methods known in the art. For example, using the known murine NGF-beta DNA sequence, one may prepare a probe to screen appropriate cell cultures for homologous mRNA. Once isolated, the mRNA may be reverse-transcribed and inserted into a cloning vector by conventional methods. See for example, R. H. Edwards et al, *Nature* (1986) 319:784–87, incorporated herein by reference. The available cDNA can also be used to obtain genomic sequence from the relevant species (M. J. Selby et al, *Mol Cell Biol* (1987) 7:3057–64). Once the sequence has been suitably amplified, it may be transferred to an appropriate expression vector, preferably a eukaryotic expression vector.

Selection of the particular expression vector depends upon the particular host used. For example, plasmids and synthetic chromosomes are used advantageously with yeast, recombinant baculovirus with insect cell cultures, and viruses (e.g., vaccinia: see U.S. Pat. No. 4,603,112, incorporated herein by reference) with mammalian cell cultures. The expression vector preferably includes at least one regulatory element, which enables one to induce and/or suppress the expression of the introduced NGF-beta gene. Thus, one may grow the host culture to a desired density prior to expressing the NGF-beta gene and harvesting the product.

Most mammalian cells are capable of expressing NGF (R. H. Edwards et al, "The Regulation of NGF Synthesis and Secretion in Mammalian Cells," submitted for publication).

Thus, when mammalian cells are used as the expression host, the protein recovered is likely to be processed by endogenous proteases. It is critical that the final NGF produced be the cleaved, mature hormone because cleavage activates its biological function (R. H. Edwards et al, "Processing of the native NGF Precursor to Form Biologically Active NGF," in press). If the expression host produces its own NGF, the expressed product is likely to contain a small amount of contaminating host NGF. Thus, it is preferred to employ as expression hosts either hosts which do not express NGF (e.g., non-vertebrates such as filamentous fungi, yeast, insect cell culture, etc.), or hosts which naturally produce NGF-beta of the same type (e.g., using human cell culture to express human NGF-beta). The latter approach is mainly applicable where the exogenous NGF-beta is unmodified (i.e., is unchanged in sequence).

In the practice of the invention, one may cleave and activate the pro-NGF-beta to the mature form either before or after isolation from the expression host. Thus, one may use nucleotide sequences encoding NGF-gamma or another processing enzyme, and so provide for coexpression of the pro-NGF-beta with intracellular processing of the pro-NGF-beta. Alternatively, one may simply isolate the expressed pro-NGF-beta, and produce the active form by treatment with a stoichiometric amount of NGF-gamma or a catalytic amount of trypsin. Trypsin is preferred, for reasons of economy, but a number of other enzymes would serve equally well.

The resulting active NGF-beta is then purified by conventional techniques. Purification from non-recombinant sources is described in the literature (see e.g., K. Suda et al, *Proc Nat Acad Sci U.S.A.*, (1978) 75:4042–46). Because expression inside cells seems to be an effective way to produce active precursor that can be properly cleaved and activated, translocation across the endoplasmic reticulum membrane probably plays a role in correct folding. (R. H. Edwards, *J Biol Chem*, in press). We accordingly express NGF as a secreted protein, greatly simplifying purification. Medium from cells expressing NGF can be filtered using a Pellicon device to retain only proteins >5 Kd. The concentrated medium will then be applied to a carboxymethylcellulose resin and eluted at high pH. This ion-exchange column has a high affinity and is known to resolve well NGF-beta, probably because of its high isoelectric point (9.1). It will also concentrate the material further, and this can be separated from any remaining contaminants by reverse-phase ($C_{18}$) HPLC, which does not reduce the biological activity of NGF-beta.

NGF-beta is preferably administered topically, or by parenteral means, including subcutaneous and intramuscular injection, injection into the CNS, implantation of sustained-release depots, intravenous injection, intranasal administration, intraventricular infusion, and the like. When used to treat nerves severed by trauma, it may be advantageous to apply NGF-beta directly to the wound, e.g., during surgery to correct other damage resulting from the trauma. Accordingly, NGF-beta may be administered as a pharmaceutical composition comprising mature, active NGF-beta in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Alternatively, one may incorporate or encapsulate NGF-beta in a suitable polymer matrix or membrane, thus providing a sustained-release delivery device suitable for implantation near the site to be treated locally. Other devices include indwelling catheters and devices such as the Alzet® minipump. Further, one may provide NGF-beta in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of NGF-beta required to treat any particular neural disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, however, a dosage of about 10 ng to 10 ug/Kg, administered intraventricularly or intrathecally over one week, for an average of about 50 ng to about 50 ug/Kg/day given intravenously, is suitable for treatment of degenerative diseases of the CNS. For treatment of severed nerves, e.g., during reattachment of a severed digit, an amount of about 50 ng to about 5 ug, administered in 0–5 mL of gelatin directly to the site before closure is sufficient.

C. Examples

The following examples are presented in further illustration, but not limitation, of the invention.

EXAMPLE 1

(Cloning of mNGF)

(A) RNA was prepared from male mouse submaxillary gland in guanidinium isothiocyanate, precipitated in lithium chloride, and extracted and reprecipitated in ethanol. Poly-A+ RNA was selected on oligo-dT-cellulose. Reverse transcriptase was employed to prepare a cDNA first strand from the RNA using random calf thymus DNA primers. The RNA-cDNA hybrid was tailed with dG and terminal transferase. Oligo-dC in a molar ration of 2:1 relative to the first strand was used to prime second-strand synthesis following the method of Okayama and Berg, *Molec Cell Biol*, (1982) 2:161–70. The ends of the double-stranded cDNA were made blunt first with Klenow enzyme, then with T4 DNA polymerase. Next, an EcoRI linker adapter was added, and the sequence inserted into a Lgt10 vector, following the method of Huynk et al, "DNA Cloning Techniques: A Practical Approach" (Glover, ed.) pp. 49–78 (IRL Press, Oxford, 1984). In vitro packaging yielded a library of about $10^6$ recombinants. The library was then screened with a probe of the sequence GGGGCTGGATGGCATGCT. Several positive clones were selected and subcloned into M13, and the nucleotide sequence determined by dideoxy sequencing in both directions.

(B) Similarly, proceeding as in part A above, human, bovine, and equine NGF-beta cDNA libraries are prepared and cloned.

(C) In most vertebrate tissues, NGF expression is so low (less than one transcript per cell) as to make cDNA libraries an unreliable source for the NGF-beta coding sequence. The murine cDNA can in such cases be used as a probe for the genomic NGF-beta sequences in man. In fact, the human NGF-beta sequences encode all of pro-NGF-beta is within one exon and one can thus simply clone the sequence into an expression vector.

EXAMPLE 2

(In vitro Expression)

This preparation describes the expression of mouse pro-NGF-beta using an in vitro expression system, for comparison with active NGF-beta of the instant invention.

The cDNA prepared in Example 1 above was cleaved with SmaI (at +66) and PstI (at +1027), following the manufacturer's directions. The cDNA may optionally be partially cleaved with BstXI (+184), then PstI, removing part of the leader sequence prior to insertion. The cleaved cDNA is then inserted into a pSP65 riboprobe vector and amplified. The pSP65 vector is next linearized with HindIII downstream from the stop codon, and used as a template for mRNA synthesis using SP6 polymerase, ribonucleotides, and 7mGpppG (P. A. Kreig et al, *Nucleic Acids Res* (1984) 12:7057–70).

The resulting mRNAs were then translated in vitro using wheat germ in the presence of $^{35}$S-methionine (A. H. Erickson et al, *Meth Enzym* (1983) 96:38–50).

EXAMPLE 3

(Cloning of NGF-beta in Vaccinia)

Initial attempts to induce expression of NGF-beta using plasmids containing the NGF-beta gene under the control of a number of viral and cellular 5' flanking sequences, and with a selectable marker, were uniformly unsuccessful. We were, however, able to obtain satisfactory expression using a vaccinia vector. Two constructs were prepared: a long construct encoding both AUG start codons ("A"), and a shorter sequence encoding only the downstream AUG ("B"). The translation products of A and B are two alternate forms of pro-NGF-beta, both of which are cleaved by NGF-gamma or trypsin to provide NGF-beta.

Construct A was prepared by cleaving NGF-beta cDNA (as prepared in Example 1) alternately with SmaI and PstI. Construct B was prepared by cleaving NGF-beta cDNA with ApaI and PstI. The ends of the fragments were filled in and made blunt with T4 DNA polymerase. Plasmid pVV3 was cleaved with BamHI, the ends made blunt, and the NGF-beta cDNA ligated in, as shown in FIG. 1. (In the Figure, TK represents the vital thymidine kinase gene, and 7.5K represents the TK 5' flanking sequence.) The NGF cDNA is positioned between the 5' and 3' ends of the vaccinia TK gene. Transfection with this recombinant plasmid into cells infected with the wild type virus (VV:wt) results in homologous recombination into the viral TK gene, thus rendering the virus TK$^-$. These TK$^-$ virons are selected in bromodeoxyuridine, and plaques hybridizing with the NGF-beta cDNA are selected. The resulting recombinant viruses were denoted W:NGF-A and W:NGF-B.

EXAMPLE 4

(Expression of Active NGF-beta)

Mouse L929 fibroblasts were grown in Dulbecco's modified Eagle medium (DME-H21) with 10% fetal calf serum (FCS) at 37° C. The cells were inoculated at a multiplicity of infection of 10–20 in phosphate-buffered saline (PBS), 1 mM MgCl$_2$, and 0.01% bovine serum albumin (BSA). After incubation at room temperature for one hour, the medium was replaced with DME-H21 containing 10% FCS and incubated an additional hour at 37° C. Cells were harvested by scraping, washed in PBS, resuspended in 50 mM NaCl/ 100 mM Tris (pH 7.6), and disrupted by sonication, or by two cycles of freezing and thawing. The lysates were cleared of particulate material by centrifugation for 15 min at 4° C. in a microcentrifuge to provide a pro-NGF-beta solution.

EXAMPLE 5

(Digestion of Pro-NGF-beta)

(A) NGF-gamma for processing pro-NGF-beta was purified from murine saliva. Mouse saliva was induced with epinephrine and collected in glass capillary tubes, and the 7S NGF purified by gel filtration HPLC. The 7S complex ran as an easily separable 100 Kd peak on Superose (Pharmacia). Conventional ion exchange chromatography at pH 4 on carboxymethylcellulose allowed the isolation of individual NGF subunits (S. Varon et al, *Biochemistry* (1968) 7:1296–1303). Purified alpha and gamma subunits were dialyzed against 50 mM Tris, pH 7.6, and stored at –20° C. The enzymatic activity of NGF-gamma may be assayed fluorometrically by using the synthetic substrate D-val-leu-arg-N-fluorocoumarin.

16 mm wells confluent with L929 cells were infected with VV:NGF-A, VV:NGF-B, or W:wt, as described above, labeled for 30 min., harvested, and digested with NGF-gamma for 20 min. at 37° C. in 100 mM Tris, pH 7.6. Each lane of wells received 0, 9, 90, 900, or 1800 ng of NGF-gamma. The proteins were then immunoprecipitated with anti-NGF, and analyzed on a 12.5% polyacrylamide gel. The gel results demonstrate the production of pure, active NGF-beta.

(B) Similarly, proceeding as in part (A) above but substituting 0, 0.58, 5.8, and 58 ng of trypsin (obtained from Sigma) for NGF-gamma, mature, active NGF-beta was prepared.

(C) Similarly, proceeding as in part (A) above, pro-NGF-beta prepared in vitro as described in Example 2 above was substituted for pro-NGF-beta prepared in vivo. Upon digestion with NGF-gamma as described in part (A), the pro-NGF-beta was degraded, as shown by analysis on 12.5% polyacrylamide gel.

(D) Similarly, proceeding as in part (B) above, pro-NGF-beta prepared in vitro as described in Example 2 above was substituted for pro-NGF-beta prepared in vivo. Upon digestion with trypsin as described in part (B), the pro-NGF-beta was degraded, as shown by analysis on 12.5% polyacrylamide gel.

EXAMPLE 6

(Demonstration of Activity)

Activity of NGF-beta is demonstrated by applying a sample to dissociated chick dorsal root ganglia, then counting the number of neuronal cells exhibiting processes larger than the cell body, as described by R. J. Riopelle et al, *Canad J Physiol Pharmacol* (1982) 60:707–714, incorporated herein by reference.

Pro-NGF-beta purified from mouse L929 cells infected with W:NGF-A and W:NGF-B was digested with trypsin (100 ng trypsin/50 ug pro-NGF-beta) in 100 mM Tris, pH 7.6, at 37° C. for 30 min. The trypsin was then inactivated, and the solution applied to dissociated chick dorsal root ganglia cells. After 18–24 hours, the presence of cell processes larger than the cell bodies was determined. Appropriate positive and negative controls were also included, using L929 supernatant from cells infected with VV:wt, supernatants from L929 infected with W:NGF-A or VV:NGF-B but not digested, and purified mouse (non-recombinant) NGF-beta. Antisera to NGF fully blocked the activity seen from this preparation.

The results indicate that supernatant from L929/VV:wt exhibited no NGF activity, supernatant from L929/VV:NGF-A and L929/W:NGF-B (not digested) exhibited little to no activity, and supernatant from L929/VV:NGF-A and L929/W:NGF-B digested with trypsin exhibited substantial NGF-beta activity.

EXAMPLE 7

(Expression in Yeast)

One may advantageously express pro-NGF-beta in yeast, for large-scale fermentation.

Using standard techniques, cDNA (as prepared in Example 1 above) is cleaved with SmaI (at +66) and PstI (at +1027), following the manufacturer's directions. The ends of the fragments are then filled in and made blunt with T4 DNA polymerase. A suitable yeast plasmid, for example YRp7 (ATCC No. 37060) is then cleaved downstream from the 2 micron promoter (e.g., with BamHI), the ends made blunt, and the NGF-beta cDNA ligated in. The resulting plasmid is then transformed into a suitable yeast strain, e.g., *Saccharomyces carlsbergensis*, and cultured using methods known generally in the art. The resulting transformed host expresses pro-NGF-beta, which may be cleaved to provide active, mature NGF-beta using NGF-gamma or trypsin, as described above.

(B) Optionally, one may also transform the host with a plasmid encoding NGF-gamma or trypsin, thus providing a host capable of expressing mature NGF-beta. Preferably, the pro-NGF-beta sequence and the processing enzyme sequence are under the control of appropriate promoters, allowing one to express each protein in appropriate amounts.

EXAMPLE 8

(Formulations)

(A) An NGF-beta formulation suitable for administration by injection is prepared as follows:

| | |
|---|---|
| NGF-beta | 1–100 ug |
| HSA | 100 mg |
| Phosphate-buffered saline qs | 100 mL |

The components are simply mixed, sterile filtered, and packaged under sterile conditions.

(B) An NGF-beta "depot" formulation is prepared as follows:

| | |
|---|---|
| NGF-beta | 1–100 ug |
| HSA | 100.0 mg |
| Methylcellulose | 3.0 g |
| Methyl- and propyl parabens | 0.2 g |
| Water for injection qs | 100.0 mL |

The methylcellulose and parabens are dissolved in 90 mL of the water to provide a gel, to which is added the NGF-beta and HSA suspended in the remaining 10 mL.

What is claimed:

1. A process for preparing biologically active recombinant NGF-beta, which comprises:

(a) expressing a gene encoding pro-NGF-beta in a eukaryotic expression host into which DNA comprising said gene and at least one regulatory element has been introduced; and (b) treating said pro-NFD-beta so produced with a trypsin like protease to yield biologically active recombinant NGF-beta.

2. The process of claim 1 wherein said eukaryotic expression host is mammalian.

3. The process of claim 1 wherein said eukaryotic expression host is yeast.

4. The process of claim 2 wherein said protease is trypsin in a catalytic amount.

5. The process of claim 2 wherein said protease is NGF-gamma in a stoichiometric amount.

* * * * *